(12) United States Patent
Leanna et al.

(10) Patent No.: US 8,696,732 B2
(45) Date of Patent: Apr. 15, 2014

(54) STENT DELIVERY SYSTEM

(75) Inventors: Gary J. Leanna, Holden, MA (US);
Michal Weisman, Palo Alto, CA (US);
Eric Schneider, Lincoln, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 126 days.

(21) Appl. No.: 13/189,707

(22) Filed: Jul. 25, 2011

(65) Prior Publication Data

US 2012/0035700 A1 Feb. 9, 2012

Related U.S. Application Data

(60) Provisional application No. 61/370,530, filed on Aug. 4, 2010.

(51) Int. Cl.
*A61F 2/06* (2013.01)

(52) U.S. Cl.
USPC .......................................... 623/1.11

(58) Field of Classification Search
USPC ................ 606/139, 142, 200; 623/1.11, 2.11
See application file for complete search history.

(56) References Cited

U.S. PATENT DOCUMENTS

| | | | |
|---|---|---|---|
| 4,382,445 A | 5/1983 | Sommers | |
| 4,592,341 A | 6/1986 | Omagari et al. | |
| 4,699,611 A | 10/1987 | Bowden | |
| 4,931,037 A | 6/1990 | Wetterman | |
| 4,950,228 A | 8/1990 | Knapp, Jr. et al. | |
| 4,955,858 A | 9/1990 | Drews | |
| 4,957,479 A | 9/1990 | Roemer | |
| 4,973,301 A | 11/1990 | Nissenkorn | |
| 4,990,133 A | 2/1991 | Solazzo | |
| 5,052,998 A | 10/1991 | Zimmon | |
| 5,152,749 A | 10/1992 | Giesy et al. | |
| 5,160,341 A | 11/1992 | Brenneman et al. | |
| 5,334,185 A | 8/1994 | Giesy et al. | |
| 5,372,600 A | 12/1994 | Beyar et al. | |
| 5,401,257 A | 3/1995 | Chevalier, Jr. et al. | |
| 5,507,464 A | 4/1996 | Hamerski et al. | |
| 5,599,291 A | 2/1997 | Balbierz et al. | |
| 5,681,274 A | 10/1997 | Perkins et al. | |
| 5,690,643 A | 11/1997 | Wijay | |
| 5,746,769 A * | 5/1998 | Ton et al. ...................... | 606/206 |
| 5,921,952 A | 7/1999 | Desmond, III et al. | |
| 5,921,971 A | 7/1999 | Agro et al. | |
| 6,245,076 B1 | 6/2001 | Yan | |
| 6,248,100 B1 | 6/2001 | de Toledo et al. | |

(Continued)

FOREIGN PATENT DOCUMENTS

EP 1872749 1/2008

*Primary Examiner* — Corrine M McDermott
*Assistant Examiner* — Alexander Orkin
(74) *Attorney, Agent, or Firm* — Seager, Tufte & Wickhem LLC

(57) ABSTRACT

A drainage stent delivery system including an elongate shaft of a medial device, a drainage catheter or stent, and a retention mechanism for selectively retaining the drainage stent on the elongate shaft. The tubular stent is positioned on and surrounding the elongate shaft. The elongate shaft includes a distal tip portion which is deflectable from a first position to a second position, the distal tip portion of the elongate shaft being biased toward the first position. Deflecting the distal tip portion of the elongate shaft from the first position to the second position moves the distal tip portion toward the central longitudinal axis of the tubular stent to allow the stent to be decoupled from the elongate shaft.

10 Claims, 13 Drawing Sheets

(56) References Cited

U.S. PATENT DOCUMENTS

| | | |
|---|---|---|
| 6,264,624 B1 | 7/2001 | Desmond, III et al. |
| 6,562,024 B2 | 5/2003 | Alvarez de Toledo et al. |
| 6,620,191 B1 | 9/2003 | Svensson |
| 7,198,637 B2 | 4/2007 | Deshmukh et al. |
| 7,208,008 B2 * | 4/2007 | Clarke ................... 623/1.11 |
| 7,658,747 B2 * | 2/2010 | Forde et al. .............. 606/200 |
| 7,763,008 B2 | 7/2010 | Yu |
| 7,879,080 B2 | 2/2011 | Sato |
| 2003/0047654 A1 | 3/2003 | Johansson et al. |
| 2004/0153123 A1 * | 8/2004 | Palermo et al. .......... 606/213 |
| 2005/0085891 A1 | 4/2005 | Goto et al. |
| 2005/0085892 A1 | 4/2005 | Goto et al. |
| 2006/0068144 A1 | 3/2006 | Mizuno et al. |
| 2006/0276873 A1 | 12/2006 | Sato |
| 2007/0179588 A1 * | 8/2007 | Balgobin .................. 623/1.11 |
| 2008/0004685 A1 | 1/2008 | Seemann et al. |
| 2008/0234814 A1 * | 9/2008 | Salahieh et al. ......... 623/2.11 |

* cited by examiner

STENT DELIVERY SYSTEM

CROSS REFERENCE TO RELATED APPLICATIONS

This application claims the benefit of U.S. Provisional Application No. 61/370,530, filed Aug. 4, 2010, the entire disclosure of which is incorporated herein by reference.

TECHNICAL FIELD

The disclosure is directed to a stent delivery system. More particularly, the disclosure is directed to a retention structure for selectively retaining a stent to a shaft of a stent delivery system. Specifically, the disclosure is directed to a retention structure for selectively retaining a drainage stent to a catheter shaft of a drainage stent delivery system.

BACKGROUND

Medical devices, such as catheters, are widely used in various medical procedures to access remote anatomical locations and/or deploy therapeutic devices. One exemplary catheter system is a drainage stent delivery system configured to deliver a drainage stent (e.g., a drainage catheter) to a body lumen, such as a lumen of the biliary tree or a ureter. It may be desirable to releasably connect the drainage stent to the delivery system in order to provide the medical personnel with control over positioning and deployment of the drainage catheter in a body lumen without premature deployment of the drainage stent from the delivery system. Some exemplary drainage stent delivery systems including features for releasably connecting a drainage stent to a delivery system are disclosed in U.S. Pat. Nos. 5,921,952 and 6,562,024, the disclosures of which are incorporated herein by reference. For instance, a releasable connecting feature in the form of a flexible thread or suture may be used for releasably connecting the drainage stent to a shaft of the drainage stent delivery system.

However, a need remains to provide alternative embodiments of a retention system to releasably retain a stent, such as a vascular stent or a drainage stent, or other endoprosthesis to a stent delivery system, such as a vascular stent or drainage stent delivery system, which allows controlled positioning and deployment of the stent in a body lumen.

SUMMARY

The disclosure is directed to several alternative designs and configurations of medical device structures and assemblies including a retention structure for selectively retaining a stent to a delivery system.

Accordingly, one illustrative embodiment is a stent delivery system including a medical device including an elongate shaft extending distally from a proximal end to a distal tip portion. A tubular stent is positioned on and surrounding the elongate shaft. The distal tip portion of the medical device is deflectable from a first position to a second position, the distal tip portion of the medical device being biased toward the first position. Deflecting the distal tip portion of the medical device from the first position to the second position moves the distal tip portion toward the central longitudinal axis of the tubular stent. In some instances, the distal tip portion may be located distal of the distal end of the tubular stent when the tubular stent is retained on the elongate shaft.

Another illustrative embodiment is a stent delivery system including a medical device including an elongate shaft extending distally from a proximal end to a distal tip portion. A tubular stent is positioned on and surrounding the elongate shaft such that the distal tip portion of the medical device is located distal of the distal end of the tubular stent. The distal tip portion of the medical device is deflectable from a first position to a second position, the distal tip portion of the elongate shaft being biased toward the first position. In the first position the distal tip portion has an outer diameter greater than the inner diameter of the distal end of the tubular stent, and in the second position the distal tip portion has an outer diameter less than or equal to the inner diameter of the distal end of the tubular stent. During deployment of the stent the distal tip portion of the medical device is deflected from the first position to the second position to allow the distal tip portion of the medical device to pass proximally through the tubular stent.

Yet another illustrative embodiment is a method of selectively disengaging a stent from an elongate shaft of a medical device. The method includes positioning a tubular stent relative to the elongate shaft of the medical device such that a distal tip portion of the medical device extends radially outward of a central longitudinal axis of the tubular stent beyond an inner diameter of a distal end of the tubular stent when the distal tip portion is in a first position. The distal tip portion of the medical device may be deflected toward the central longitudinal axis of the tubular stent such that the distal tip portion is deflected from the first position to a second position. The elongate shaft may be withdrawn proximally of the tubular stent while the distal tip portion of the medical device is in the second position in which the distal tip portion is deflected toward the central longitudinal axis of the tubular stent.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
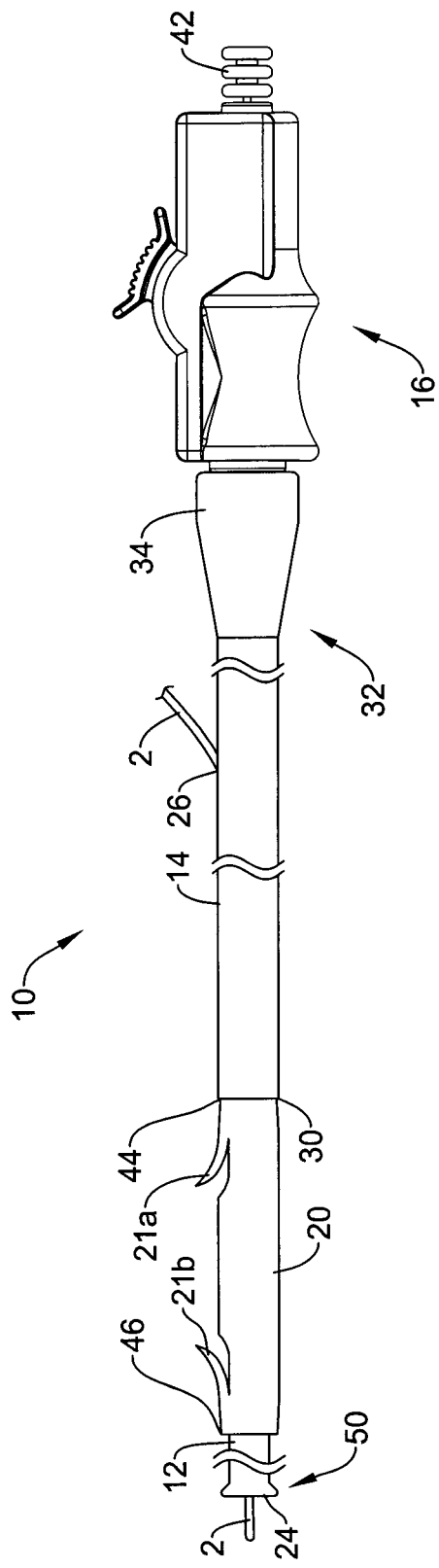
FIG. 1 is a plan view of an exemplary drainage stent delivery system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the term "proximal" refers to a direction that is generally toward a physician during a medical procedure, while the term "distal" refers to a direction that is generally toward a target site within a patient's anatomy during a medical procedure.

As used in this specification and the appended claims, the term "body lumen" means any body passage cavity that conducts fluid, including but not limited to biliary ducts, pancreatic ducts, ureteral passages, esophagus, and blood vessels such as those of the human vasculature system.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
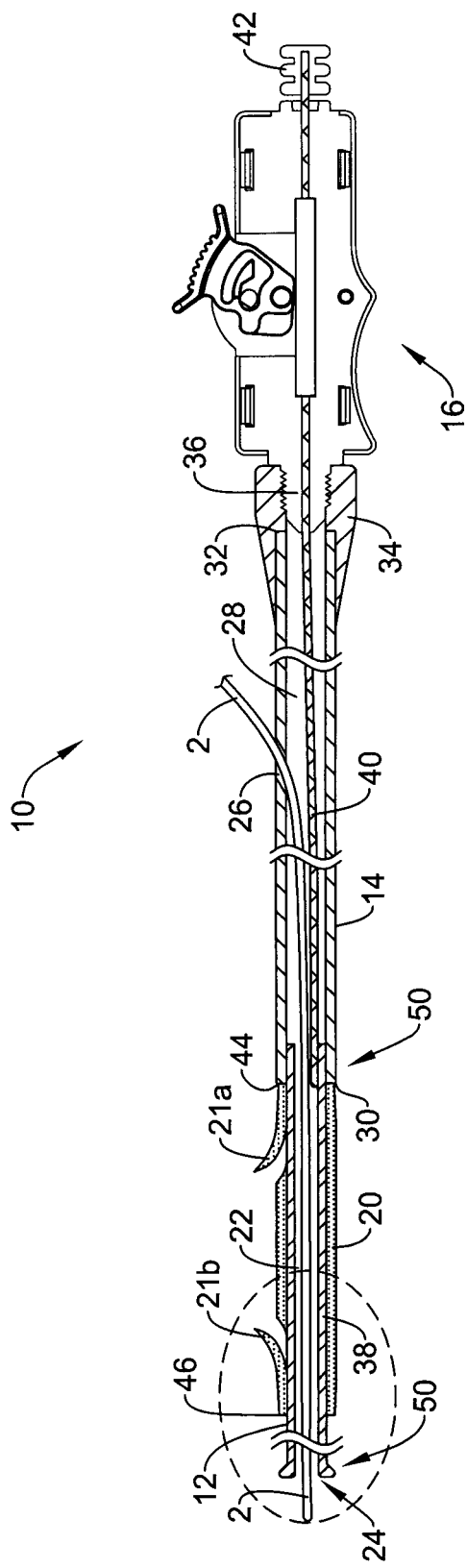
FIG. 2 is a longitudinal cross-sectional view of the drainage stent delivery system of FIG. 1.

Referring now to FIGS. 1 and 2, there is shown an exemplary medical device, illustrated as a drainage stent delivery system 10 for delivering a drainage catheter or stent 20 to an anatomical location, such as in a lumen of the biliary tree or a ureter. The drainage stent 20 may be used to bypass or drain an obstructed lumen and can be configured for long-term positioning within the lumen. The drainage stent 20 may be an to elongate tubular member which is generally not expandable. The drainage stent 20 may have a proximal end 44, a distal end 46 and a lumen 48 extending through the drainage stent 20 from the proximal end 44 to the distal end 46. In some embodiments, the drainage stent 20 may include one or more, or a plurality of barbs 21, or other retention features that may help prevent migration of the drainage stent 20 when positioned in a body lumen. The illustrated drainage stent 20 includes a proximal barb 21a and a distal barb 21b. It should be understood that the terms "drainage catheter" and "drainage stent" can be used interchangeably with reference to these applications.

The drainage stent delivery system 10 is designed for use with a conventional guidewire 2 and may include a drainage stent 20, a guide catheter 12, a push catheter 14, and a handle assembly 16. The guidewire 2 may extend into a lumen 22 of the guide catheter 12 through a distal guidewire port 24 and out a proximal guidewire port 26 in a sidewall of the push catheter 14, providing the drainage stent delivery system 10 with single-operator-exchange (SOE) capabilities.

The guide catheter 12 may be slidably disposed in the lumen 28 of the push catheter 14 and extend distally from the distal end 30 of the push catheter 14. The guide catheter 12 may extend through the drainage stent 20 to a location distal of the drainage stent 20. In some embodiments, a distal portion of the push catheter 14, or a component thereof, may extend into the lumen of the drainage stent 20. In some instances, the proximal end 44 of the drainage stent 20 may abut and/or face a distal end or rim 30 of the push catheter 14, or a component thereof, while a distal portion or component of the push catheter 14 extends into the lumen of the drainage stent 20. In other embodiments, the push catheter 14, or a component thereof, may extend over the drainage stent 20, surrounding a portion of the drainage stent 20.

The drainage stent delivery system 10 may include a means for releasably connecting the drainage stent 20 to an elongate shaft of the drainage stent delivery system 10, such as the guide catheter 12 or the push catheter 14 of the drainage stent delivery system 10. When the drainage stent 20 has been properly placed, the drainage stent 20 may be disconnected from the drainage stent delivery system 10 such that the drainage stent 20 remains in the lumen when the guide catheter 12 and/or the push catheter 14 are withdrawn. Some exemplary retention mechanisms for selectively coupling the drainage stent 20 to an elongate shaft of the drainage stent delivery system 10 are further described herein. The retention mechanisms may be used to selectively deploy, reposition and/or retrieve the drainage stent 20 during a medical procedure.

The proximal end 32 of the push catheter 14 may be attached to the handle assembly 16. For example, the proximal end 32 may include a female luer lock connector 34 threadably coupled to a threaded male connector 36 of the handle assembly 16. It is understood, however, that the push catheter 14 may be attached to the handle assembly 16 and extend distally therefrom by other means, such as adhesive bonding, welding, friction fit, interlocking fit, or other suitable means. In some instances, a component of the push catheter 14 may be longitudinally (e.g., slidably and/or rotatably) actuatable relative to another component of the push catheter 14. In such embodiments, the handle assembly 16 may be configured such that the actuatable component of the push catheter 14 may be actuated by medical personnel while the stationary component of the push catheter 14 remains stationary relative to the handle assembly 16.

The guide catheter 12 may include a distal tubular portion 38 and a proximal elongate wire 40, such as a pull wire, coupled to the distal tubular portion 38. The elongate wire 40 may be coupled to the distal tubular portion 38 at a coupling location. The elongate wire 40 may extend through the lumen 28 of the push catheter 14 to the handle assembly 16 while the distal tubular portion 38 extends through the drainage stent 20 to a location distal of the drainage stent 20. In some embodiments, the elongate wire 40 may extend through the handle assembly 16 to a location proximal of the handle assembly 16.

The proximal end of the elongate wire 40 may terminate at a knob 42 which may be grasped by an operator to manipulate the guide catheter 12.

As shown in FIG. 2, the elongate wire 40 may share the lumen 28 of the push catheter 14 with the guidewire 2 along a portion of the length of the elongate wire 40. Thus, a portion of the elongate wire 40 may extend proximally from the tubular portion 38 along the side of the guidewire 2 through the lumen 28 of the push catheter 14 up to a location where the guidewire 2 exits the proximal guidewire port 26 of the push catheter 14.

During a medical procedure, the drainage stent delivery system 10 may be advanced to a target location in the anatomy of a patient. For instance, the drainage stent delivery system 10 may be advanced over the guidewire 2 to a target location. In some instances, the drainage stent delivery system 10 may be tracked over the guidewire 2 as the drainage stent delivery system 10 is advanced through a working channel of an endoscope. The guidewire 2 may pass through the lumen 22 of the guide catheter 12 and the lumen 28 of the push catheter 14 and exit through the proximal guidewire port 26 of the push catheter 14.

When the drainage stent 20 has been positioned at the target location in a lumen, the operator may then selectively disengage the drainage stent 20 from the drainage stent delivery system 10 and withdraw the drainage stent delivery system 10, or components thereof, proximally relative to the drainage stent 20 to deploy the drainage stent 20 at the target location. For instance, in some embodiments axial movement of an elongate shaft of the drainage stent delivery system 10 (e.g., the guide catheter 12 and/or the push catheter 14) relative to the drainage stent 20 may disengage or unlock the drainage stent 20 from the drainage stent delivery system 10. Once the drainage stent 20 is disengaged from the guide catheter 12 and/or the push catheter 14, withdrawing the guide catheter 12 and/or the push catheter 14 proximally may release the drainage stent 20 from the drainage stent delivery system 10 in order to deploy the drainage stent 20 at the target location. Once the drainage stent 20 has been properly deployed at the target location, the drainage stent delivery system 10 may then be withdrawn. In some instances, the drainage stent delivery system 10 may also be used to reposition and/or retrieve the drainage stent 20 during a medical procedure.

Some exemplary retention structures for selectively coupling the drainage stent 20 to a component, such as an elongate shaft, of the drainage stent delivery system 10 will now be further described.

Figure 3A:
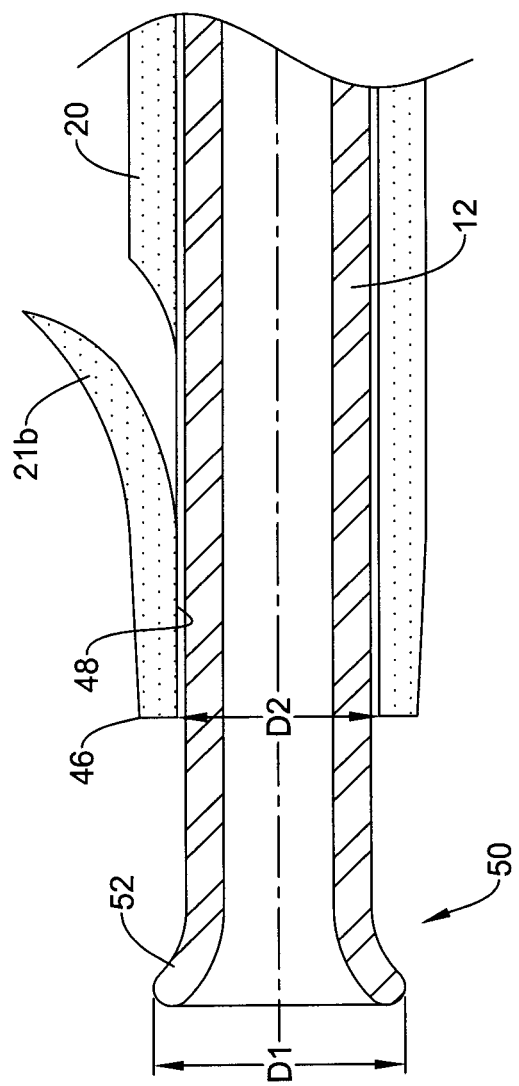
FIGS. 3A and 3B are longitudinal cross-sectional views illustrating the functionality of an exemplary retention structure for selectively retaining a stent to an elongate shaft of a delivery system.
Figure 3B:
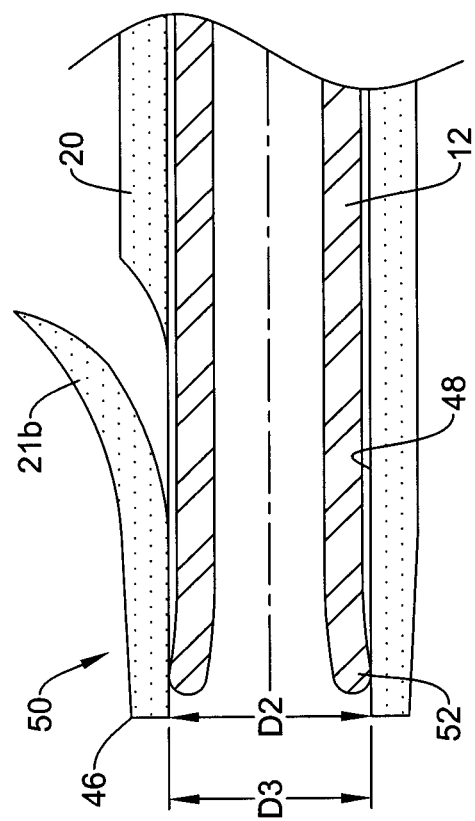

FIGS. 3A and 3B illustrate the functionality of a first exemplary retention structure for selectively retaining the drainage stent 20 on an elongate shaft of the drainage stent delivery system 10. Although the drainage stent 20 is illustrated as being selectively coupled to the guide catheter 12 of the drainage stent delivery system 10, it is understood that in some embodiments the drainage stent 20 may be selectively coupled to another elongate shaft in the manner described with regard to FIGS. 3A and 3B.

FIG. 3A illustrates the drainage stent 20 positioned on and surrounding the elongate shaft of the guide catheter 12 in which the drainage stent 20 is retained on the guide catheter 12. As shown in FIG. 3A, the guide catheter 12 extends through the lumen 48 of the drainage stent 20 such that the distal tip portion 50 of the guide catheter 12 is located distal of the distal end 46 of the drainage stent 20.

The distal tip portion 50 of the guide catheter 12 may be a flared portion 52 flared radially outward toward the distal extremity of the guide catheter 12. The flared portion 52 may be a unitary portion of the elongate shaft of the guide catheter 12, or the flared portion 52 may be a separate component attached to the elongate shaft of the guide catheter 12. The diameter of the lumen through the guide catheter 12 throughout the flared portion 52 may be enlarged relative to the diameter of the lumen proximal of the flared portion 52. For instance, the lumen through the flared portion 52 may taper radially outward from a proximal extent of the flared portion 52 to a distal extent of the flared portion 52. The distal tip portion 50 may be flexible to allow deflection of the distal tip portion 50 when a force is applied to the distal tip portion 50. The distal tip portion 50 may have an outer diameter D1 in an equilibrium first position which is greater than the inner diameter D2 of the distal end 46 of the drainage stent 20. Thus, the distal tip portion 50 may extend radially outward of the central longitudinal axis of the drainage stent 20 beyond the inner diameter D2 of the distal end 46 of the drainage stent 20 when the distal tip portion 50 is in the first position.

The distal tip portion 50 may be deflectable or radially collapsible toward the central longitudinal axis of the drainage stent 20 from the first position to a second position shown in FIG. 3B. The distal tip portion 50 may be biased toward the first position, thus when an applied force is removed from the distal tip portion 50, the distal tip portion 50 may automatically revert back to the first position.

When the distal tip portion 50 is deflected or radially collapsed toward the central longitudinal axis of the drainage stent 20, the distal tip portion 50 may have an outer diameter D3 less than or equal to the inner diameter D2 of the distal end 46 of the drainage stent 20. In the second position, the guide catheter 12 may be withdrawn proximally from the drainage stent 20 as the distal tip portion 50 passes into and through the lumen 48 of the drainage stent 20 in order to decouple the drainage stent 20 from the guide catheter 12.

An axial force may be applied to the guide catheter 12 to deflect or collapse the distal tip portion 50 toward the central longitudinal axis of the drainage stent 20. For example, the guide catheter 12 may be actuated proximally relative to the push catheter 14 and the drainage stent 20 to move the distal tip portion 50 into engagement with the distal end 46 of the drainage stent 20. Further movement of the guide catheter 12 proximally causes the distal end 46 of the drainage stent 20 to exert a corresponding force on the distal tip portion 50, causing the distal tip portion 50 to deflect or collapse radially inward toward the central longitudinal axis as the distal tip portion 50 is pulled against the distal end 46 of the drainage stent 20. An axial force greater than a threshold level is necessary to deflect or collapse the distal tip portion 50 a sufficient amount to allow the distal tip portion 50 to be drawn into the distal end 46 of the drainage stent 20. For instance, the distal tip portion 50 may be configured such that an axial force of less than 2 pounds applied to the guide catheter 12 is insufficient to deflect the distal tip portion 50 from the first position in which the distal tip portion 50 has an outer diameter D1 greater than the inner diameter D2 of the distal end 46 of the drainage stent 20 to the second position in which the distal tip portion 50 has an outer diameter D3 less than or equal to the inner diameter D2 of the distal end 46 of the drainage stent 20. The distal tip portion 50 may be configured such that an axial force greater than 2 pounds, for example, an axial force of about 3 pounds to about 4 pounds, may be sufficient to deflect the distal tip portion 50 from the first position to the second position. The threshold level of force needed to deflect or collapse the distal tip portion 50, and thus decouple the drainage stent 20 from the guide catheter 12 may be chosen depending on the medical application. For example, the threshold level may be greater than resistance forces exerted on the drainage stent 20 during normal positioning, repositioning and/or retrieval procedures. In some instances, the threshold level may be 2 pounds, 3 pounds, 4 pounds or more depending on the level of retention desired.

Thus, when a sufficient axial force is applied to the guide catheter 12, the distal end 46 of the drainage stent 20 pushes against the distal tip portion 50 to urge the distal tip portion 50 from the first position, shown in FIG. 3A, to the second position, shown in FIG. 3B, to allow the distal tip portion 50 to enter into the lumen 48 of the drainage stent 20 and ultimately be withdrawn proximally of the drainage stent 20. Thus, the axial force applied to withdraw the guide catheter 12 from the drainage stent 20 must be sufficiently large to overcome the restoring forces of the distal tip portion 50 tending to revert the distal tip portion 50 back to the equilibrium first position.

The distal tip portion 50 may be designed to collapse when the desired tensile force is applied. In some instances, the distal tip portion 50 may include a thinner wall thickness than an adjacent portion and/or the rest of the guide catheter 12, or the distal tip portion may be formed with a weaker or more flexible material than an adjacent portion and/or the rest of the guide catheter 12.

Figure 3C:
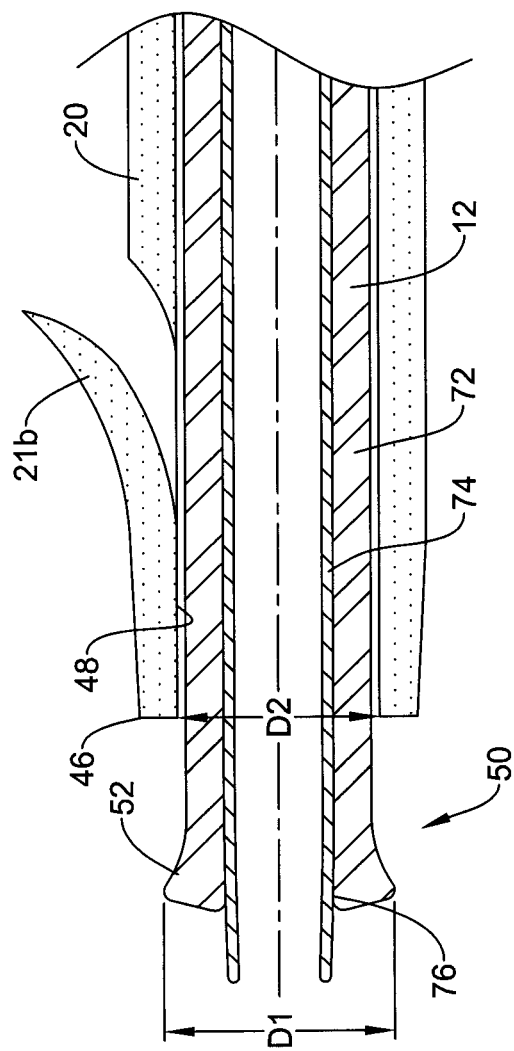
FIGS. 3C and 3D are longitudinal cross-sectional view illustrating the functionality of an alternative configuration of the retention structure of FIGS. 3A and 3B for selectively retaining a stent to an elongate shaft of a delivery system.
Figure 3D:
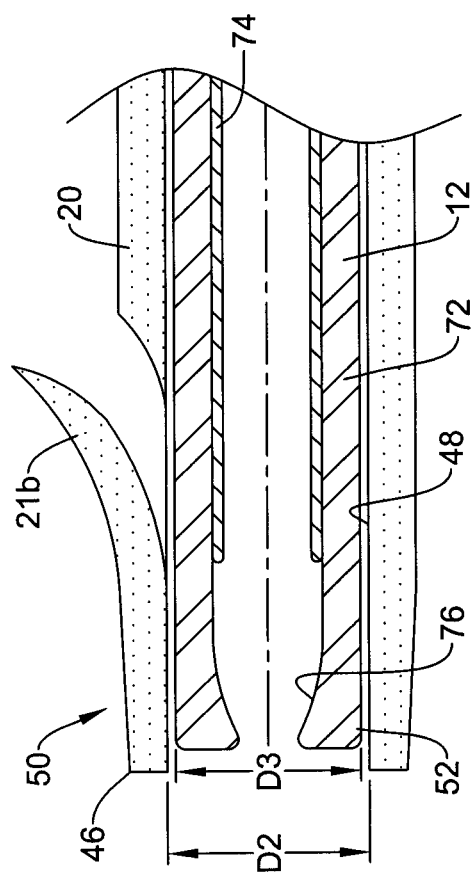

FIGS. 3C and 3D illustrate the functionality of an alternative configuration of the retention structure of FIGS. 3A and 3B for selectively retaining the drainage stent 20 to an elongate shaft of the drainage stent delivery system 10. In this configuration, the guide catheter 12 may include first and second coaxial components which may be longitudinally actuated relative to one another. For example, the guide catheter 12 may include an outer tubular member 72 and an inner member 74, which may also be tubular to receive the guidewire 2 therethrough, extending through the outer tubular member 72. The outer tubular member 72 and/or the inner member 74 may be actuated at the handle assembly 16 to effect relative actuation between the outer tubular member 72 and the inner member 74.

The distal tip portion 50 of the outer tubular member 72 may be expanded or flared outward when the inner member 74 is positioned in the distal tip portion 50. Withdrawal of the inner member 74 proximally may allow the distal tip portion 50 to deflect or collapse radially inward to deploy the drainage stent 20. For instance, the distal tip portion 50 may include a ramp 76 against which the inner member 74 presses against to urge the distal tip portion 50 radially outward.

As shown in FIG. 3C, the distal tip portion 50 may have an outer diameter D1 in a first position which is greater than the inner diameter D2 of the distal end 46 of the drainage stent 20. Thus, the distal tip portion 50 may extend radially outward of the central longitudinal axis of the drainage stent 20 beyond the inner diameter D2 of the distal end 46 of the drainage stent 20 when the distal tip portion 50 is in the first position.

The distal tip portion 50 may be configured to deflect or radially collapse toward the central longitudinal axis of the drainage stent 20 from the first position to a second position shown in FIG. 3D when the inner member 74 is actuated proximally. The distal tip portion 50 may be biased toward the second position, thus when inner member 74 removed from the distal tip portion 50, the distal tip portion 50 may automatically revert back to the second position.

When the distal tip portion 50 is deflected or radially collapsed toward the central longitudinal axis of the drainage stent 20, the distal tip portion 50 may have an outer diameter D3 less than or equal to the inner diameter D2 of the distal end 46 of the drainage stent 20. In the second position, the guide catheter 12 may be withdrawn proximally from the drainage stent 20 as the distal tip portion 50 passes into and through the lumen 48 of the drainage stent 20 in order to decouple the drainage stent 20 from the guide catheter 12.

In other embodiments the inner member 74 may be attached to the outer tubular member 72 such that actuation of the inner member 74 relative to the outer tubular member 72 may cause the distal tip portion 50 to deflect or collapse radially inward.

Figure 4A:
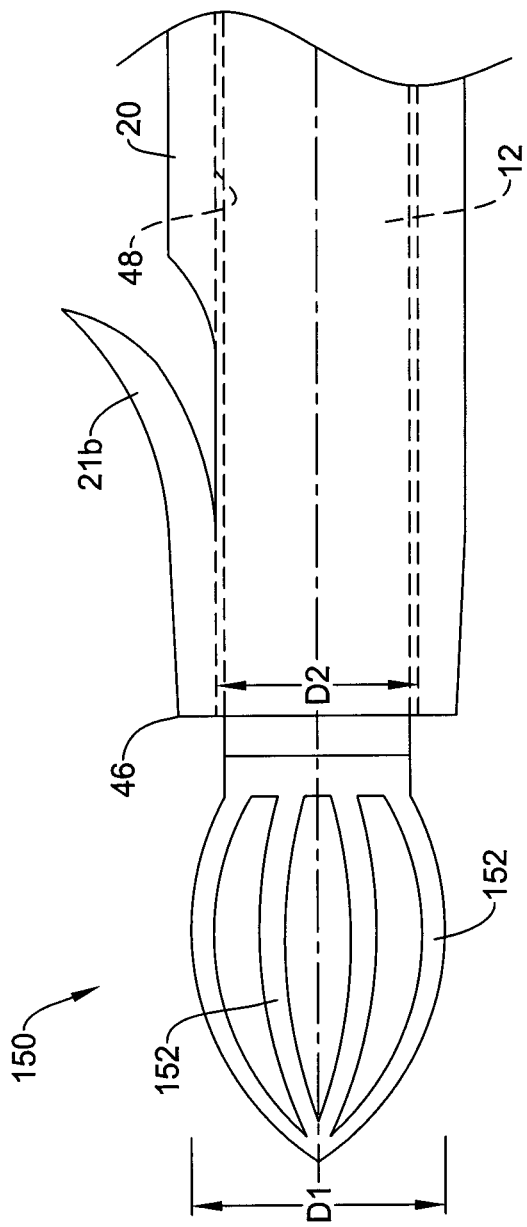
FIGS. 4A and 4B are plan views illustrating the functionality of another retention structure for selectively retaining a stent to an elongate shaft of a delivery system.
Figure 4B:
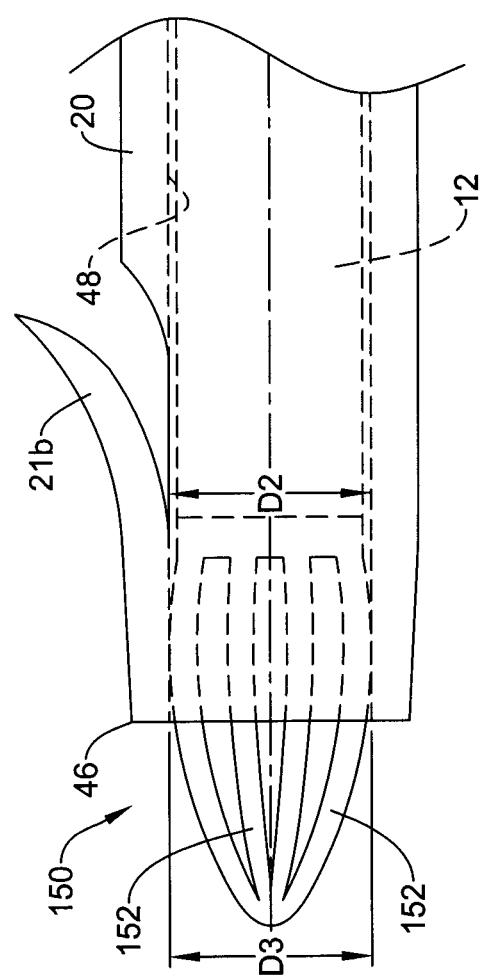

FIGS. 4A and 4B illustrate the functionality of another exemplary retention structure for selectively retaining the drainage stent 20 on an elongate shaft of the drainage stent delivery system 10. Although the drainage stent 20 is illustrated as being selectively coupled to the guide catheter 12 of the drainage stent delivery system 10, it is understood that in some embodiments the drainage stent 20 may be selectively coupled to another elongate shaft in the manner described with regard to FIGS. 4A and 4B.

FIG. 4A illustrates the drainage stent 20 positioned on and surrounding the elongate shaft of the guide catheter 12 in which the drainage stent 20 is retained on the guide catheter 12. As shown in FIG. 4A, the guide catheter 12 extends through the lumen 48 of the drainage stent 20 such that the distal tip portion 150 of the guide catheter 12 is located distal of the distal end 46 of the drainage stent 20.

The distal tip portion 150 of the guide catheter 12 may include one or more, or a plurality of collapsible ribs 152 spaced from one another. The collapsible rib(s) 152 may be a unitary portion of the elongate shaft of the guide catheter 12, or the collapsible rib(s) 152 may be a separate component attached to the elongate shaft of the guide catheter 12. For instance, in some embodiments the collapsible rib(s) 152 may be a portion of the tubular wall of the guide catheter 12 after slits or slots have been formed through the tubular wall of the guide catheter 12. In some instances, the collapsible ribs 152 may collectively form a bulbous tip portion of the guide catheter 12 in which the proximal ends of the collapsible ribs 152 extend distally from the tubular wall of the guide catheter 12 and the distal ends of the collapsible ribs 152 converge and are joined or coupled together at a distal tip. The distal tip portion 150 may be flexible to allow deflection of the distal tip portion 150 when a force is applied to the distal tip portion 150. The distal tip portion 150 may have an outer diameter D1 in an equilibrium first position which is greater than the inner diameter D2 of the distal end 46 of the drainage stent 20. Thus, the distal tip portion 150 may extend radially outward of the central longitudinal axis of the drainage stent 20 beyond the inner diameter D2 of the distal end 46 of the drainage stent 20 when the distal tip portion 150 is in the first position.

The distal tip portion 150 may be deflectable or radially collapsible toward the central longitudinal axis of the drainage stent 20 from the first position to a second position shown in FIG. 4B. The distal tip portion 150 may be biased toward the first position, thus when an applied force is removed from the distal tip portion 150, the distal tip portion 150 may automatically revert back to the first position.

When the distal tip portion 150 is deflected or radially collapsed toward the central longitudinal axis of the drainage stent 20, the distal tip portion 150 may have an outer diameter D3 less than or equal to the inner diameter D2 of the distal end 46 of the drainage stent 20. In the second position, the guide catheter 12 may be withdrawn proximally from the drainage stent 20 as the distal tip portion 150 passes into and through the lumen 48 of the drainage stent 20 in order to decouple the drainage stent 20 from the guide catheter 12.

An axial force may be applied to the guide catheter 12 to deflect or collapse the distal tip portion 150 toward the central longitudinal axis of the drainage stent 20. For example, the guide catheter 12 may be actuated proximally relative to the push catheter 14 and the drainage stent 20 to move the distal tip portion 150 into engagement with the distal end 46 of the drainage stent 20. Further movement of the guide catheter 12 proximally causes the distal end 46 of the drainage stent 20 to exert a corresponding force on the distal tip portion 150, causing the distal tip portion 150 to deflect or collapse radially inward toward the central longitudinal axis as the distal tip portion 150 is pulled against the distal end 46 of the drainage stent 20. An axial force greater than a threshold level is necessary to deflect or collapse the distal tip portion 150 a sufficient amount to allow the distal tip portion 150 to be drawn into the distal end 46 of the drainage stent 20. For instance, the distal tip portion 150 may be configured such that an axial force of less than 2 pounds applied to the guide catheter 12 is insufficient to deflect the distal tip portion 150 from the first position in which the distal tip portion 150 has an outer diameter D1 greater than the inner diameter D2 of the distal end 46 of the drainage stent 20 to the second position in which the distal tip portion 150 has an outer diameter D3 less than or equal to the inner diameter D2 of the distal end 46 of the drainage stent 20. The distal tip portion 150 may be configured such that an axial force greater than 2 pounds, for example, an axial force of about 3 pounds to about 4 pounds, may be sufficient to deflect the distal tip portion 150 from the first position to the second position. The threshold level of force needed to deflect or collapse the distal tip portion 150, and thus decouple the drainage stent 20 from the guide catheter 12 may be chosen depending on the medical application. For example, the threshold level may be greater than resistance forces exerted on the drainage stent 20 during normal positioning, repositioning and/or retrieval procedures. In some instances, the threshold level may be 2 pounds, 3 pounds, 4 pounds or more depending on the level of retention desired.

Thus, when a sufficient axial force is applied to the guide catheter 12, the distal end 46 of the drainage stent 20 pushes against the distal tip portion 150 to urge the distal tip portion 150 from the first position, shown in FIG. 4A, to the second position, shown in FIG. 4B, to allow the distal tip portion 150 to enter into the lumen 48 of the drainage stent 20 and ultimately be withdrawn proximally of the drainage stent 20. Thus, the axial force applied to withdraw the guide catheter 12 from the drainage stent 20 must be sufficiently large to overcome the restoring forces of the distal tip portion 150 tending to revert the distal tip portion 150 back to the equilibrium first position.

In some instances, the embodiment illustrated in FIGS. 4A and 4B may alternatively use first and second coaxial components (e.g., an outer tubular member and an inner member) which may be longitudinally actuated relative to one another at the handle assembly 16 to effect relative actuation between the first and second coaxial components. Relative actuation between the outer tubular member and the inner member may cause the distal tip portion 150 to collapse or deflect radially inward to effect deployment of the drainage stent 20 from the guide catheter 12. For example, an outer tubular member may be attached to a proximal end of the collapsible rib(s) 152 and an inner member may be attached to a distal end of the collapsible rib(s) 152. Actuation of the outer tubular member proximally and/or actuation of the inner member distally, for example, may elongate the distance between the proximal and distal ends of the collapsible rib(s), thereby collapsing or deflecting the collapsible rib(s) 152 radially inward. Alternatively, a sheath may be advanced distally over the distal tip portion 150 to collapse or deflect the distal tip portion 150 radially inward.

Figure 5A:
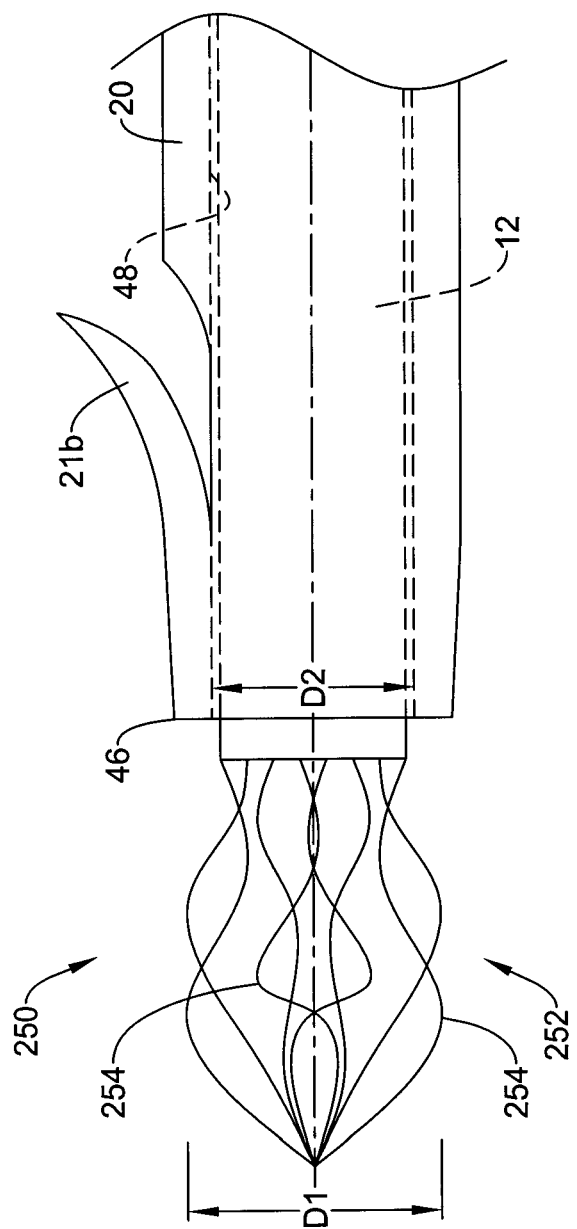
FIGS. 5A and 5B are plan views illustrating the functionality of another retention structure for selectively retaining a stent to an elongate shaft of a delivery system.
Figure 5B:
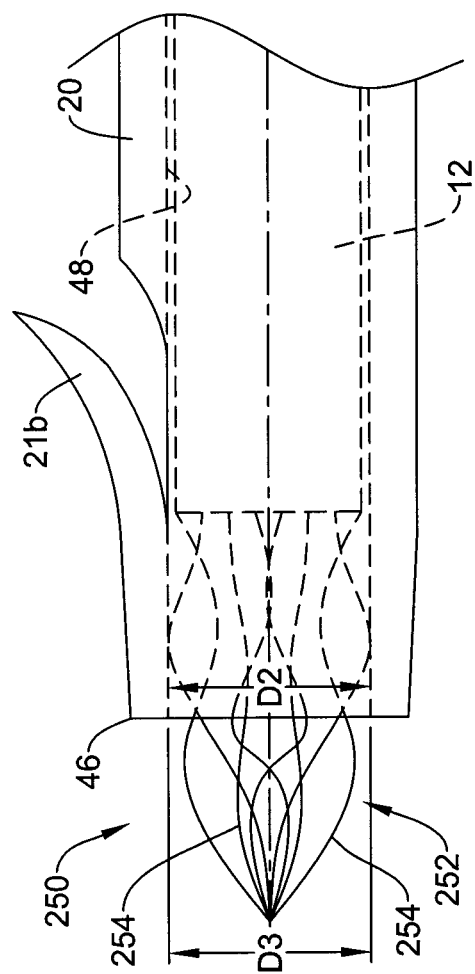

FIGS. 5A and 5B illustrate the functionality of another exemplary retention structure for selectively retaining the drainage stent 20 on an elongate shaft of the drainage stent delivery system 10. Although the drainage stent 20 is illustrated as being selectively coupled to the guide catheter 12 of the drainage stent delivery system 10, it is understood that in some embodiments the drainage stent 20 may be selectively coupled to another elongate shaft in the manner described with regard to FIGS. 5A and 5B.

FIG. 5A illustrates the drainage stent 20 positioned on and surrounding the elongate shaft of the guide catheter 12 in which the drainage stent 20 is retained on the guide catheter 12. As shown in FIG. 5A, the guide catheter 12 extends through the lumen 48 of the drainage stent 20 such that the distal tip portion 250 of the guide catheter 12 is located distal of the distal end 46 of the drainage stent 20.

The distal tip portion 250 of the guide catheter 12 may include a wire basket 252 formed with one or more wires 254. The wires 254 may be formed of any desired resilient material, such as a nickel-titanium alloy. The wires 254 of the wire basket 252 may be helically arranged or otherwise arranged to form a collapsible structure. The wire basket 252 may be attached to the elongate shaft of the delivery catheter 12 to form the distal tip portion 250. For instance, the proximal ends of the wires 254 of the wire basket 252 may be attached to and extend distally from the distal end of the delivery catheter 12 and the distal ends of the wires 254 may converge and be joined or coupled together at a distal tip. The distal tip portion 250 may be flexible to allow deflection of the distal tip portion 250 when a force is applied to the distal tip portion 250. The distal tip portion 250 may have an outer diameter D1 in an equilibrium first position which is greater than the inner diameter D2 of the distal end 46 of the drainage stent 20. Thus, the distal tip portion 250 may extend radially outward of the central longitudinal axis of the drainage stent 20 beyond the inner diameter D2 of the distal end 46 of the drainage stent 20 when the distal tip portion 250 is in the first position.

The distal tip portion 250 may be deflectable or radially collapsible toward the central longitudinal axis of the drainage stent 20 from the first position to a second position shown in FIG. 5B. The distal tip portion 250 may be biased toward the first position, thus when an applied force is removed from the distal tip portion 250, the distal tip portion 250 may automatically revert back to the first position.

When the distal tip portion 250 is deflected or radially collapsed toward the central longitudinal axis of the drainage stent 20, the distal tip portion 250 may have an outer diameter D3 less than or equal to the inner diameter D2 of the distal end 46 of the drainage stent 20. In the second position, the guide catheter 12 may be withdrawn proximally from the drainage stent 20 as the distal tip portion 250 passes into and through the lumen 48 of the drainage stent 20 in order to decouple the drainage stent 20 from the guide catheter 12.

An axial force may be applied to the guide catheter 12 to deflect or collapse the distal tip portion 250 toward the central longitudinal axis of the drainage stent 20. For example, the guide catheter 12 may be actuated proximally relative to the push catheter 14 and the drainage stent 20 to move the distal tip portion 250 into engagement with the distal end 46 of the drainage stent 20. Further movement of the guide catheter 12 proximally causes the distal end 46 of the drainage stent 20 to exert a corresponding force on the distal tip portion 250, causing the distal tip portion 250 to deflect or collapse radially inward toward the central longitudinal axis as the distal tip portion 250 is pulled against the distal end 46 of the drainage stent 20. An axial force greater than a threshold level is necessary to deflect or collapse the distal tip portion 250 a sufficient amount to allow the distal tip portion 250 to be drawn into the distal end 46 of the drainage stent 20. For instance, the distal tip portion 250 may be configured such that an axial force of less than 2 pounds applied to the guide catheter 12 is insufficient to deflect the distal tip portion 250 from the first position in which the distal tip portion 250 has an outer diameter D1 greater than the inner diameter D2 of the distal end 46 of the drainage stent 20 to the second position in which the distal tip portion 250 has an outer diameter D3 less than or equal to the inner diameter D2 of the distal end 46 of the drainage stent 20. The distal tip portion 250 may be configured such that an axial force greater than 2 pounds, for example, an axial force of about 3 pounds to about 4 pounds, may be sufficient to deflect the distal tip portion 250 from the first position to the second position. The threshold level of force needed to deflect or collapse the distal tip portion 250, and thus decouple the drainage stent 20 from the guide catheter 12 may be chosen depending on the medical application. For example, the threshold level may be greater than resistance forces exerted on the drainage stent 20 during normal positioning, repositioning and/or retrieval procedures. In some instances, the threshold level may be 2 pounds, 3 pounds, 4 pounds or more depending on the level of retention desired.

Thus, when a sufficient axial force is applied to the guide catheter 12, the distal end 46 of the drainage stent 20 pushes against the distal tip portion 250 to urge the distal tip portion 250 from the first position, shown in FIG. 5A, to the second position, shown in FIG. 5B, to allow the distal tip portion 250 to enter into the lumen 48 of the drainage stent 20 and ultimately be withdrawn proximally of the drainage stent 20. Thus, the axial force applied to withdraw the guide catheter 12 from the drainage stent 20 must be sufficiently large to overcome the restoring forces of the distal tip portion 250 tending to revert the distal tip portion 250 back to the equilibrium first position.

In some instances, the embodiment illustrated in FIGS. 5A and 5B may alternatively use first and second coaxial components (e.g., an outer tubular member and an inner member) which may be longitudinally actuated relative to one another at the handle assembly 16 to effect relative actuation between the first and second coaxial components. Relative actuation between the outer tubular member and the inner member may cause the distal tip portion 250 to collapse or deflect radially inward to effect deployment of the drainage stent 20 from the guide catheter 12. For example, an outer tubular member may be attached to a proximal end of the wire basket 252 and an inner member may be attached to a distal end of the wire basket 252. Actuation of the outer tubular member proximally and/or actuation of the inner member distally, for example, may elongate the distance between the proximal and distal ends of the wire basket 252, thereby collapsing or deflecting the wire basket 252 radially inward. Alternatively, a sheath may be advanced distally over the distal tip portion 250 to collapse or deflect the distal tip portion 250 radially inward.

Figure 6A:
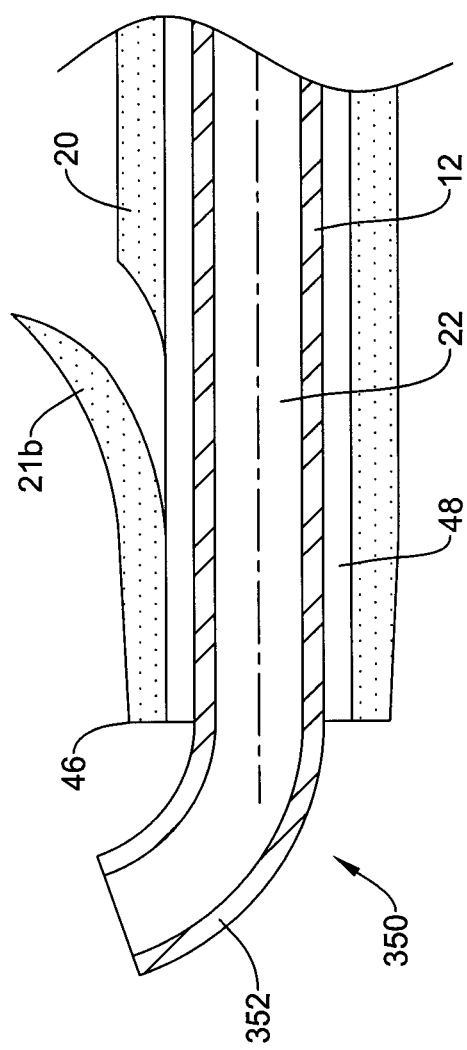
FIGS. 6A-6C are cross-sectional views illustrating the functionality of another retention structure for selectively retaining a stent to an elongate shaft of a delivery system.
Figure 6B:
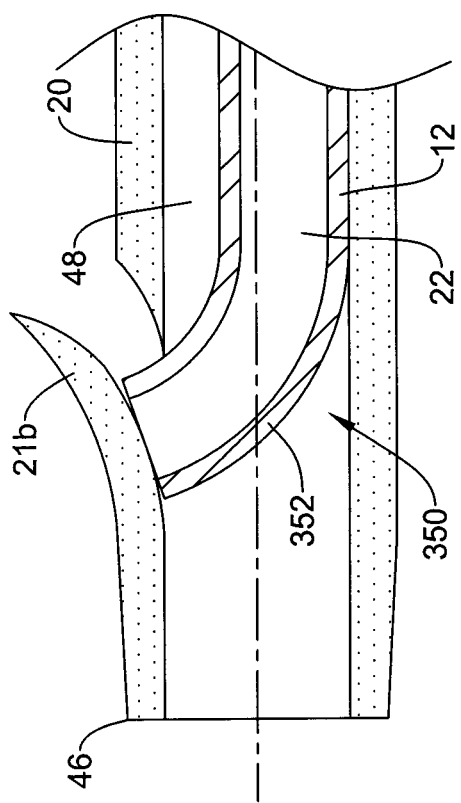
Figure 6C:
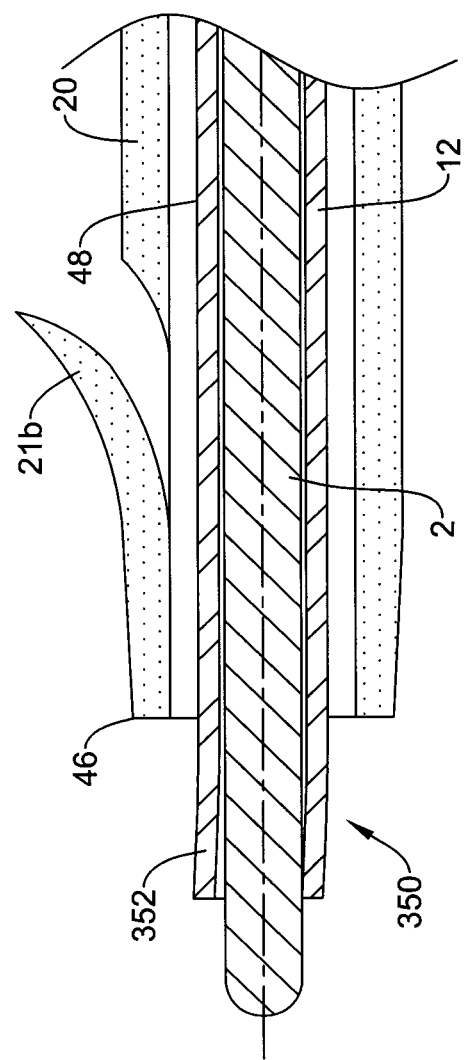

FIGS. 6A, 6B and 6C illustrate the functionality of a yet another exemplary retention structure for selectively retaining the drainage stent 20 on an elongate shaft of the drainage stent delivery system 10. Although the drainage stent 20 is illustrated as being selectively coupled to the guide catheter 12 of the drainage stent delivery system 10, it is understood that in some embodiments the drainage stent 20 may be selectively coupled to another elongate shaft in the manner described with regard to FIGS. 6A-6C.

FIG. 6A illustrates the drainage stent 20 positioned on and surrounding the elongate shaft of the guide catheter 12 in which the drainage stent 20 is retained on the guide catheter 12. As shown in FIG. 6A, the guide catheter 12 extends through the lumen 48 of the drainage stent 20 such that the distal tip portion 350 of the guide catheter 12 is located distal of the distal end 46 of the drainage stent 20.

The distal tip portion 350 of the guide catheter 12 may include a curved portion 352 curved away from the central longitudinal axis of the drainage stent 20 toward the distal extremity of the guide catheter 12. The curved portion 352, which may be a "J" hook in some instances, may be a unitary portion of the elongate shaft of the guide catheter 12, or the curved portion 352 may be a separate component attached to the elongate shaft of the guide catheter 12. In some instances, the curved portion 352 of the distal tip portion 350 may include one or more flaps or tabs, or other discrete sections curving outward from the tubular wall of the guide catheter 350.

In some instances, deflection of the curved portion 352 may be effected by material and/or design characteristics of the distal tip portion 350. For example, deflection may be effected by the wall thickness, bend angle, and/or bend radius of the curved portion 352. Additionally or alternatively, deflection may be effected by cuts, slits, slots, score lines, or other design features formed in the distal tip portion 350.

The distal tip portion 350 may be flexible to allow deflection of the distal tip portion 350 when a force is applied to the distal tip portion 350. The distal tip portion 350 may extend radially outward of the central longitudinal axis of the drainage stent 20 beyond the inner diameter D2 of the distal end 46 of the drainage stent 20 when the distal tip portion 350 is in the first position.

Alternatively, as shown in FIG. 6B, the curved portion 352 of the distal tip portion 350 may engage the opening formed through the tubular wall of the drainage stent 20 proximate the barb 21 to retain the drainage stent 20 on the guide catheter 12. In such an instance, the distal tip portion 350 may extend radially outward of the central longitudinal axis of the drainage stent 20 beyond the inner surface of the lumen 48 of the drainage stent 20 when the distal tip portion 350 is in the first position.

The distal tip portion 350 may be deflectable toward the central longitudinal axis of the drainage stent 20 from the first position to a second position shown in FIG. 6C. The distal tip portion 350 may be biased toward the first position, thus when an applied force is removed from the distal tip portion 350, the distal tip portion 350 may automatically revert back to the first position.

When the distal tip portion 350 is deflected toward the central longitudinal axis of the drainage stent 20, the distal tip portion 350 may extend radially outward of the central longitudinal axis of the drainage stent 20 less than or equal to the inner diameter D2 of the distal end 46 of the drainage stent 20 and/or less than or equal to the inner surface of the lumen 48 of the drainage stent 20. In the second position, the guide catheter 12 may be withdrawn proximally from the drainage stent 20 as the distal tip portion 350 passes into and through the lumen 48 of the drainage stent 20 in order to decouple the drainage stent 20 from the guide catheter 12.

An axial force may be applied to the guide catheter 12 to deflect the distal tip portion 350 toward the central longitudinal axis of the drainage stent 20. For example, regarding the orientation shown in FIG. 6A, the guide catheter 12 may be actuated proximally relative to the push catheter 14 and the drainage stent 20 to move the distal tip portion 350 into engagement with the distal end 46 of the drainage stent 20. Further movement of the guide catheter 12 proximally causes the distal end 46 of the drainage stent 20 to exert a corresponding force on the distal tip portion 350, causing the distal tip portion 350 to deflect toward the central longitudinal axis as the distal tip portion 350 is pulled against the distal end 46 of the drainage stent 20.

Similarly, regarding the orientation shown in FIG. 6B, the guide catheter 12 may be actuated proximally relative to the push catheter 14 and the drainage stent 20 to move the distal tip portion 350 into engagement with the proximal edge of the opening through the tubular wall of the drainage stent 20. Further movement of the guide catheter 12 proximally causes the tubular wall of the drainage stent 20 to exert a corresponding force on the distal tip portion 350, causing the distal tip portion 350 to deflect toward the central longitudinal axis as the distal tip portion 350 is pulled against the proximal edge of the opening through the tubular wall of the drainage stent 20.

An axial force greater than a threshold level is necessary to deflect the distal tip portion 350 a sufficient amount to allow the distal tip portion 350 to be drawn into the distal end 46 and/or through the lumen 48 of the drainage stent 20. For instance, the distal tip portion 350 may be configured such that an axial force of less than 2 pounds applied to the guide catheter 12 is insufficient to deflect the distal tip portion 350 from the first position in which the distal tip portion 350 extends radially greater than the inner diameter D2 of the distal end 46 of the drainage stent 20 to the second position in which the distal tip portion 350 extends radially less than or equal to the inner diameter D2 of the distal end 46 of the drainage stent 20. The distal tip portion 350 may be configured such that an axial force greater than 2 pounds, for example, an axial force of about 3 pounds to about 4 pounds, may be sufficient to deflect the distal tip portion 350 from the first position to the second position. The threshold level of force needed to deflect the distal tip portion 350, and thus decouple the drainage stent 20 from the guide catheter 12 may be chosen depending on the medical application. For example, the threshold level may be greater than resistance forces exerted on the drainage stent 20 during normal positioning, repositioning and/or retrieval procedures. In some instances, the threshold level may be 2 pounds, 3 pounds, 4 pounds or more depending on the level of retention desired.

Thus, when a sufficient axial force is applied to the guide catheter 12, the distal end 46 of the drainage stent 20 pushes against the distal tip portion 350 to urge the distal tip portion 350 from the first position, shown in FIG. 6A, to the second position to allow the distal tip portion 350 to enter into the lumen 48 of the drainage stent 20 and ultimately be withdrawn proximally of the drainage stent 20. Thus, the axial force applied to withdraw the guide catheter 12 from the drainage stent 20 must be sufficiently large to overcome the restoring forces of the distal tip portion 350 tending to revert the distal tip portion 350 back to the equilibrium first position.

Alternatively, as shown in FIG. 6C, the distal tip portion 350 may be straightened from the first position to the second position by advancing a guidewire 2, or other elongate member, through the distal tip portion 350. The guidewire 2 may have a stiffness sufficient to overcome the biasing forces of the distal tip portion 350 tending to return the distal tip portion 350 to the curved configuration of the equilibrium first position. When the distal tip portion 350 is sufficiently straightened to the second position to allow the distal tip portion 350 to be drawn into and through the lumen 48 of the drainage stent 20, the guide catheter 12 may be actuated proximally to withdraw the guide catheter 12 from the lumen 48 of the drainage stent 20, thereby deploying the drainage stent 20.

In other instances, the distal tip portion 350, which may be substantially straight in an equilibrium position, may be deflected, curved or bent radially outward by advancing a bent or curved inner member, such as the guidewire 2 having a bent or curved distal portion, or other guide member, through the distal tip portion 350 to cause the distal tip portion 350 to be deflected, curved or bent outward. The curved portion of the guidewire 2 or other guide member may have a stiffness sufficient to overcome biasing forces of the distal tip portion 350 tending to return the distal tip portion 350 to the straight, equilibrium position. Removal of the guidewire 2 or other guide member may allow the distal tip portion 350 to revert back to the straight, equilibrium position, thereby deploying the drainage stent 20.

Although the embodiments disclosed depict the collapsible or deflectable distal end portion of the guide catheter 12 located distal of the drainage stent 20, in some instances, the collapsible or deflectable portion of the guide catheter 12 may be located with the drainage stent 20 and operate to generate an interference fit with the inner surface of the drainage stent 20 until the collapsible or deflectable portion is collapsed or deflected. In such instances, a portion of the guide catheter 12 could still extend distally beyond the drainage stent 20 during delivery of the drainage stent 20 to a target location to stabilize the system. It may be possible to reposition and or remove the drainage stent 20 with such a configuration, if desired.

Although several illustrated embodiments of the disclosed stent retention structures are illustrated as being incorporated into a delivery system for delivering a drainage stent, it is understood that the stent retention structures may also be used to selectively retain other stent or endoprosthesis devices to a delivery system. For example, in some instances the stent retention structures described herein may be used to selectively retain a vascular stent to an elongate member of a delivery system for delivering the vascular stent to a target location within the vasculature of a patient.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A stent delivery system comprising:
an elongate shaft of a medical device, the elongate shaft extending distally from a proximal end to a distal tip portion; and
a tubular stent having a proximal end, a distal end and a lumen extending therethrough along a central longitudinal axis, the tubular stent positioned on and surrounding a distal tubular portion of the elongate shaft, wherein the distal tubular portion includes the distal tip portion and a lumen extending through the distal tubular portion and the distal tip portion;
wherein the distal tip portion of the medical device is deflectable from a first position to a second position, the distal tip portion of the medical device being biased toward the first position, such that when an applied force is removed from the distal tip portion, the distal tip portion automatically reverts to the first position;
wherein the distal tip portion is positioned distal of the distal end of the tubular stent in the first position;
wherein deflecting the distal tip portion of the medical device from the first position to the second position moves the distal tip portion toward the central longitudinal axis of the tubular stent;
wherein the distal tip portion is flared radially outward toward a distal extremity of the elongate shaft in the first position such that an outer diameter of a distal portion of the distal tip portion is greater than an outer diameter of a proximal portion of the distal tip portion proximal of the distal portion of the distal tip portion in the first position;

wherein the outer diameter of the distal portion of the distal tip portion and the outer diameter of the proximal portion of the distal tip portion are both greater than the diameter of the lumen of the tubular stent in the first position.

2. The stent delivery system of claim 1, wherein the flared distal tip portion of the medical device is collapsible to an outer diameter less than or equal to the distal end the diameter of the lumen of the tubular stent.

3. The stent delivery system of claim 2, wherein the lumen of the flared distal tip portion of the medical device has a diameter greater than a proximal portion of the elongate shaft proximal of the flared distal tip portion.

4. The stent delivery system of claim 1, wherein the distal tip portion of the medical device is a curved portion curving away from the central longitudinal axis of the tubular stent and the curved portion is straightened when the distal tip portion is deflected from the first position to the second position.

5. The stent delivery system of claim 1, wherein an axial force of less than 2 pounds applied to the elongate shaft is insufficient to deflect the distal tip portion from the first position to the second position, and an axial force of greater than 2 pounds applied to the elongate shaft is required to deflect the distal tip portion from the first position to the second position.

6. The stent delivery system of claim 5, wherein an axial force of about 3 pounds to about 4 pounds applied to the elongate shaft is sufficient to deflect the distal tip portion from the first position to the second position.

7. The stent delivery system of claim 1, wherein the distal tip portion is flared radially outward toward the distal extremity of the elongate shaft in the second position.

8. A stent delivery system comprising:
a push catheter having a proximal end, a distal end and a lumen extending therethrough;
a guide catheter extending through the lumen of the push catheter, the guide catheter including a tubular distal tip portion; and
a tubular stent positioned on and surrounding a portion of the guide catheter distal of the distal end of the push catheter, the tubular stent having a proximal end, a distal end and a lumen extending therethrough along a central longitudinal axis;
wherein the distal tip portion of the guide catheter is deflectable from a first position to a second position;
wherein deflecting the distal tip portion of the guide catheter from the first position to the second position moves the distal tip portion toward the central longitudinal axis of the tubular stent;
wherein the distal tip portion of the guide catheter is flared radially outward toward a distal extremity of the guide catheter such that an outer diameter of a distal portion of the distal tip portion is greater than an outer diameter of a proximal portion of the distal tip portion proximal of the distal portion of the distal tip portion in the first position;
wherein the distal tip portion is spaced distally from the distal end of the tubular stent when the distal tip portion is in the first position;
wherein the outer diameter of the distal portion of the distal tip portion and the outer diameter of the proximal portion of the distal tip portion are both greater than the diameter of the lumen of the tubular stent in the first position.

9. The stent delivery system of claim 8, wherein the distal tip portion of the guide catheter is a curved portion curving away from the central longitudinal axis of the tubular stent.

10. The stent delivery system of claim 8, wherein the distal tip portion is configured to automatically revert to the first position when an applied deflecting force is removed.

* * * * *

UNITED STATES PATENT AND TRADEMARK OFFICE
CERTIFICATE OF CORRECTION

PATENT NO.        : 8,696,732 B2
APPLICATION NO.   : 13/189707
DATED             : April 15, 2014
INVENTOR(S)       : Leanna et al.

Page 1 of 1

It is certified that error appears in the above-identified patent and that said Letters Patent is hereby corrected as shown below:

In the Claims

Column 15 Claim 2
Line 12: after "or equal to the", delete "distal end the".

Signed and Sealed this
Seventh Day of October, 2014

Michelle K. Lee
*Deputy Director of the United States Patent and Trademark Office*